(12) United States Patent
Carranza et al.

(10) Patent No.: US 6,699,244 B2
(45) Date of Patent: Mar. 2, 2004

(54) ELECTROSURGICAL INSTRUMENT HAVING A CHAMBER TO VOLATIZE A LIQUID

(75) Inventors: J. Remberto Carranza, San Francisco, CA (US); Hugh R. Sharkey, Redwood City, CA (US); John E. Ashley, San Francisco, CA (US); Gary S. Fanton, Portola Valley, CA (US)

(73) Assignee: Oratec Interventions, Inc., Menlo Park, CA (US)

(*) Notice: Subject to any disclaimer, the term of this patent is extended or adjusted under 35 U.S.C. 154(b) by 0 days.

(21) Appl. No.: 10/124,954

(22) Filed: Apr. 17, 2002

(65) Prior Publication Data

US 2003/0032954 A1 Feb. 13, 2003

Related U.S. Application Data

(63) Continuation-in-part of application No. 09/340,065, filed on Jun. 25, 1999, now Pat. No. 6,461,357, which is a continuation-in-part of application No. 09/022,612, filed on Feb. 12, 1998, now Pat. No. 6,135,999.
(60) Provisional application No. 60/037,782, filed on Feb. 12, 1997.

(51) Int. Cl.[7] ................................................. A61B 18/14
(52) U.S. Cl. ............................ 606/41; 606/45; 606/46; 606/48; 606/49; 606/50
(58) Field of Search ............................ 606/32, 41, 45, 606/46, 48, 49, 50

(56) References Cited

U.S. PATENT DOCUMENTS

| | | |
|---|---|---|
| 1,916,722 A | 7/1933 | Ende |
| 1,943,543 A | 1/1934 | McFadden |
| 2,002,594 A | 5/1935 | Wappler et al. |
| 2,004,559 A | 6/1935 | Wappler et al. |
| 2,090,923 A | 8/1937 | Wappler |
| 2,224,464 A | 12/1940 | Wolf |
| 3,856,015 A | 12/1974 | Iglesias |
| 4,033,351 A | 7/1977 | Hetzel |
| 4,362,160 A | 12/1982 | Hilterbrandt |

(List continued on next page.)

FOREIGN PATENT DOCUMENTS

| | | |
|---|---|---|
| EP | 0 542 412 | 5/1993 |
| EP | 0 558 297 | 9/1993 |
| GB | 2 160 102 A | 12/1985 |
| WO | WO 94/26228 | 11/1994 |
| WO | WO 95/10981 | 4/1995 |
| WO | WO 95/30377 | 11/1995 |
| WO | WO 95/34259 | 12/1995 |
| WO | WO 96/11638 | 4/1996 |
| WO | WO 96/32051 | 10/1996 |
| WO | WO 96/32885 | 10/1996 |
| WO | WO 96/34559 | 11/1996 |
| WO | WO 96/33914 | 12/1996 |
| WO | WO 98/07468 | 2/1998 |

*Primary Examiner*—Lee Cohen
(74) *Attorney, Agent, or Firm*—Fish & Richardson P.C.

(57) ABSTRACT

An electrosurgical instrument is provided which includes a holding formation, a probe shaft, an electric conductor, and a probe tip. The probe shaft is secured to the holding formation and has an elongated section extending therefrom. The electric conductor extends along the elongated section. The probe tip is located on a distal end of the probe shaft opposing the holding formation. The probe tip defines a volatization chamber with a mouth out of the probe tip. The probe tip includes an electrode, to which RF current is provided through the electric conductor. The electrode heats an area adjacent to the probe tip. The electrode also heats a liquid in the first volatization chamber to evaporate the liquid into a vapor pocket that ejects from the first volatization chamber through the mouth out of the probe tip. A pump effect is created so that the liquid maintains the probe tip at a more stable temperature.

25 Claims, 13 Drawing Sheets

U.S. PATENT DOCUMENTS

| | | |
|---|---|---|
| 4,651,734 A | 3/1987 | Doss et al. |
| 4,815,462 A | 3/1989 | Clark |
| 4,932,952 A | 6/1990 | Wojciechowicz, Jr. |
| 5,084,045 A | 1/1992 | Helenowski |
| 5,085,657 A | 2/1992 | Ben-Simhon |
| 5,103,804 A | 4/1992 | Abele et al. |
| 5,122,138 A * | 6/1992 | Manwaring ............ 606/49 |
| 5,152,748 A | 10/1992 | Chastagner |
| 5,171,311 A | 12/1992 | Rydell et al. |
| 5,192,267 A | 3/1993 | Shapira et al. |
| 5,192,280 A | 3/1993 | Parins |
| 5,197,964 A | 3/1993 | Parins |
| 5,206,900 A | 4/1993 | Callele |
| 5,217,459 A | 6/1993 | Kamerling |
| 5,269,780 A | 12/1993 | Roos |
| 5,281,216 A | 1/1994 | Klicek |
| 5,282,799 A | 2/1994 | Rydell |
| 5,311,858 A | 5/1994 | Adair |
| 5,318,564 A | 6/1994 | Eggers |
| 5,364,395 A | 11/1994 | West, Jr. |
| 5,451,224 A | 9/1995 | Goble et al. |
| 5,480,397 A | 1/1996 | Eggers et al. |
| 5,480,398 A | 1/1996 | Eggers |
| 5,593,406 A | 1/1997 | Eggers et al. |
| 5,681,282 A | 10/1997 | Eggers et al. |
| 5,681,308 A | 10/1997 | Edwards et al. |
| 5,683,366 A | 11/1997 | Eggers et al. |
| 5,688,270 A | 11/1997 | Yates et al. |
| 5,693,052 A | 12/1997 | Weaver |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,700,262 A | 12/1997 | Acosta et al. |
| 5,702,390 A | 12/1997 | Austin et al. |
| 5,718,702 A | 2/1998 | Edwards |
| 5,766,153 A | 6/1998 | Eggers et al. |
| 5,810,764 A | 9/1998 | Eggers et al. |
| 5,810,809 A | 9/1998 | Rydell |
| 5,836,947 A | 11/1998 | Fleischman et al. |
| 5,843,080 A | 12/1998 | Fleenor et al. |
| 5,855,061 A | 1/1999 | Malis et al. |
| 6,014,579 A | 1/2000 | Pomeranz et al. |
| 6,109,268 A | 8/2000 | Thapliyal et al. |
| 6,149,620 A | 11/2000 | Baker et al. |
| 6,273,886 B1 | 8/2001 | Edwards et al. |
| 6,332,880 B1 | 12/2001 | Yang et al. |
| 6,355,032 B1 | 3/2002 | Hovda et al. |
| 6,379,350 B1 * | 4/2002 | Sharkey et al. ............ 606/41 |
| 2001/0031963 A1 | 10/2001 | Sharkey et al. |
| 2003/0036753 A1 * | 2/2003 | Morgan et al. ............ 606/41 |

* cited by examiner

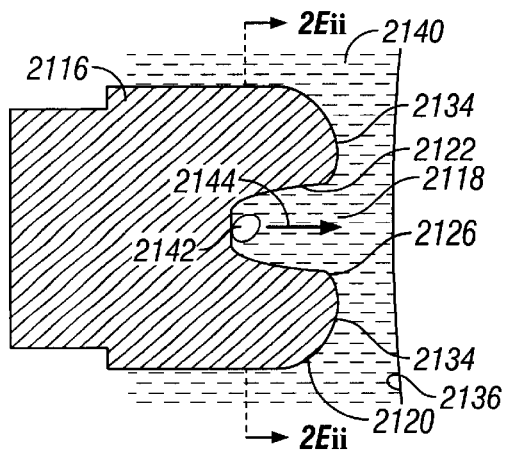
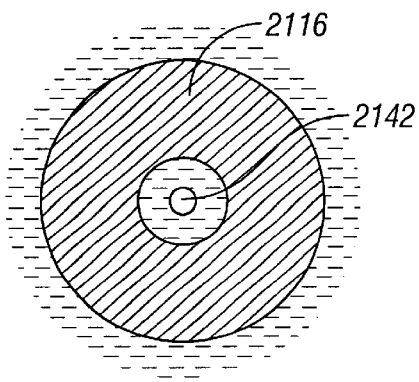
FIG. 2Ei  FIG. 2Eii
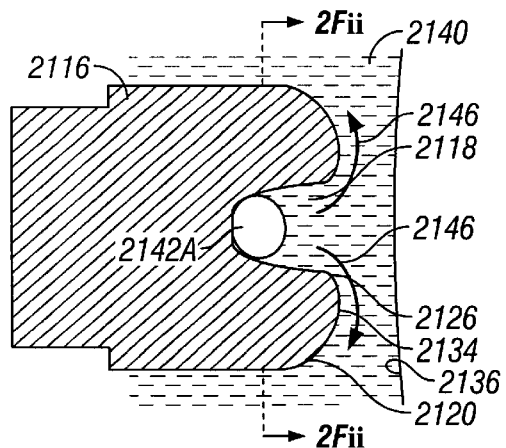
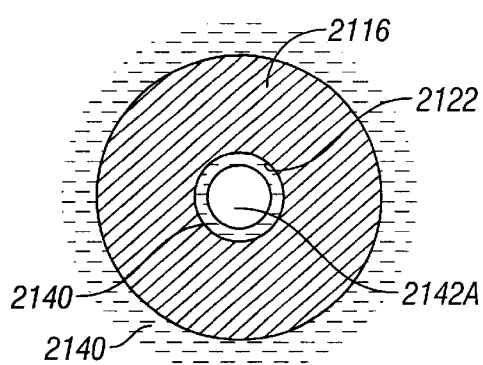
FIG. 2Fi  FIG. 2Fii
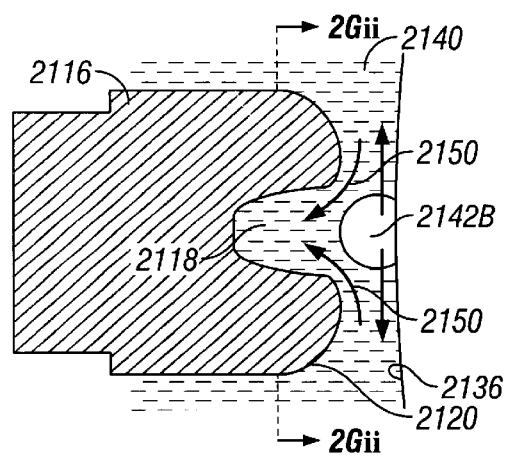
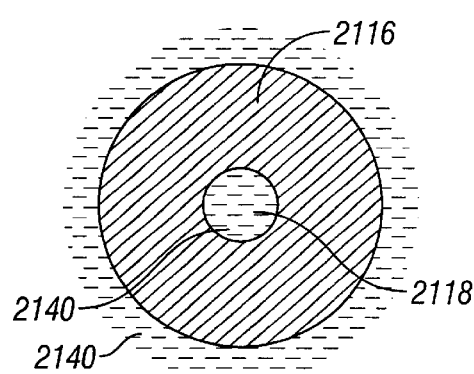
FIG. 2Gi  FIG. 2Gii

ELECTROSURGICAL INSTRUMENT HAVING A CHAMBER TO VOLATIZE A LIQUID

CROSS-REFERENCE TO RELATED APPLICATIONS

This is a continuation-in-part of Ser. No. 09/340,065, filed on Jun. 25, 1999 now U.S. Pat. No. 6,461,357, which is a continuation-in-part of Ser. No. 09/022,612 now U.S. Pat. No. 6,135,999, filed on Feb. 12, 1998, which claims priority from provisional patent application No. 60/037,782, filed on Feb. 12, 1997, all of which are incorporated herein by reference in their entirety.

BACKGROUND OF THE INVENTION

1) Field of the Invention

The invention relates to surgical systems applying thermal energy to biological tissue to modify the characteristics of the tissue. More particularly, the invention is directed to electrosurgical probes utilizing radio frequency (RF) energy to cut, coagulate, and/or ablate the tissue during a medical procedure for treatment and therapy.

2) Discussion of Related Art

Arthroscopic surgery is becoming increasingly popular, because it generally does less damage, is less invasive, and is safer than open procedures, and produces less scarring in and around joints. This type of surgery further results in a faster healing response and a quicker return of the patient to full productivity while reducing costs of open surgical procedures.

Arthroscopic surgery is usually performed with an electrosurgical instrument having a handle, a rigid elongated probe extending from the handle, and an electrode on a tip of the probe. A surgeon, holding the handle, inserts the tip into a body of a patient and positions the tip adjacent to a surgical site. RF current is then provided to the electrode to heat a fluid in an area adjacent to the tip and the surgical site.

A problem with an electrosurgical instrument of this kind is that the temperature of the electrode tends to fluctuate as a liquid circulates over the surgical site and over the electrode. What is needed is an electrosurgical instrument of this kind having a probe tip with a more stable temperature.

BRIEF SUMMARY OF THE INVENTION

According to one aspect of the invention, an electrosurgical instrument is provided which includes a holding formation, a probe shaft, an electric conductor, and a probe tip. The probe shaft is secured to the holding formation and has an elongated section extending therefrom. The electric conductor extends along the elongated section. The probe tip is located on a distal end of the probe shaft opposing the holding formation. The probe tip defines at least a first volatization chamber with a mouth out of the probe tip. The probe tip includes at least one electrode, to which RF current is provided through the electric conductor. The electrode heats an area adjacent to the probe tip. The electrode also heats a liquid in the first volatization chamber to evaporate the liquid into a vapor pocket that ejects from the first volatization chamber through the mouth out of the probe tip.

The holding formation may be a handle.

The probe shaft may be substantially rigid to allow a surgeon to move the probe tip into position without a guide.

The electric conductor may be attached to the electrode.

An inner surface of the electrode may define the volatization chamber.

Preferably, at least one cross-section through the probe tip and the volatization chamber shows no openings from the volatization chamber out of the probe tip.

The electrode may have an exposed outer surface around the volatization chamber. The exposed outer surface may entirely surround the volatization chamber.

The electrode may have a front face around the mouth. The front face may entirely surround the mouth.

The volatization chamber may have a larger cross-sectional area than the mouth.

The electrode may be a power electrode, and the probe tip may further include a ground electrode electrically connected to the power electrode through more of the liquid.

The electrosurgical instrument may further include a ground conductor extending along the elongated section and electrically attached to the ground electrode.

The electrosurgical instrument may further include a thermocouple attached to the probe tip, and a thermocouple wire extending from the thermocouple along the elongated section.

The probe tip may have at least a second volatization chamber therein. The electrode may heat more of the liquid in the second volatization chamber. The second volatization chamber may have a separate mouth out of the probe tip than the first volatization chamber. The second volatization chamber may be a ring around the first volatization chamber.

According to another aspect of the invention, an electrosurgical instrument is provided having a probe tip including an electrode to which current is provided through an electric conductor, the electrode having an exposed face with at least a first recessed volatization chamber formed therein.

According to another aspect of the invention, a method of treating a surgical site within a body of a patient is provided. A probe tip is inserted into a surgical port formed in the body of the patient until the probe tip is positioned adjacent to the surgical site. The surgical port is at least partially filled with a liquid. The liquid enters the volatization chamber in the probe tip. RF current is provided to the electrode. The electrode heats an area adjacent to the probe tip. The electrode also heats the liquid in the volatization chamber. The liquid in the volatization chamber evaporates into a vapor pocket which ejects from a mouth of the volatization chamber out of the probe tip.

The vapor pocket is preferably contained in the volatization chamber for a period of time, to allow for growth of the vapor pocket.

BRIEF DESCRIPTION OF THE DRAWINGS

The invention is described by way of examples with reference to the accompanying drawings, wherein:

FIGS. 2E(i)–2G(ii) are views illustrating the use of the probe tip, with FIGS. 2E(i), 2F(i), and 2G(i) being cross-sectional side views, and 2E(ii), 2F(ii), and 2G(ii) being cross-sectional end views taken along lines 2E(ii), 2F(ii), and 2G(ii) in FIGS. 2E(i), 2F(i), and 2G(i), respectively;

FIGS. 3A–D are side, end, perspective, and cross-sectional side views of a probe tip having an electrode with a flat face, with FIG. 3B being taken along line 3B in FIG. 3A;

FIGS. 4A–E are side, end, perspective, and cross-sectional side views of two probe tips, each having two vapor pocket chambers, with FIG. 4B being taken along line 4B in FIG. 4A;

FIGS. 11A–D are side, end, perspective, and cross-sectional side views of a probe tip having structures and features that promote unidirectional flow of liquid into the probe tip and volatize liquid out of the probe tip, with FIG. 11B being taken along line 11B in FIG. 11A.

DETAILED DESCRIPTION OF THE INVENTION

Figure 1A:
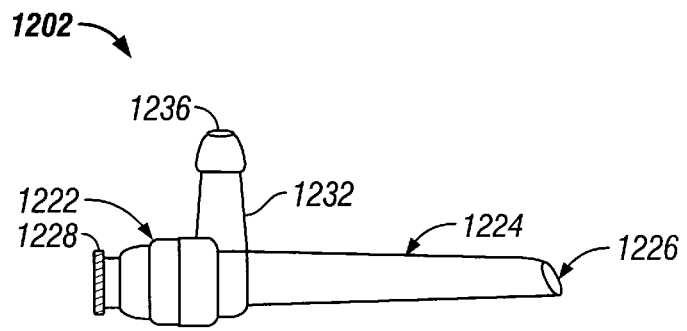
FIGS. 1A–C are a side view of an RF probe, a side view of an operating cannula, and a cross-sectional side view of the shaft portion of the RF probe, respectively.
Figure 1B:
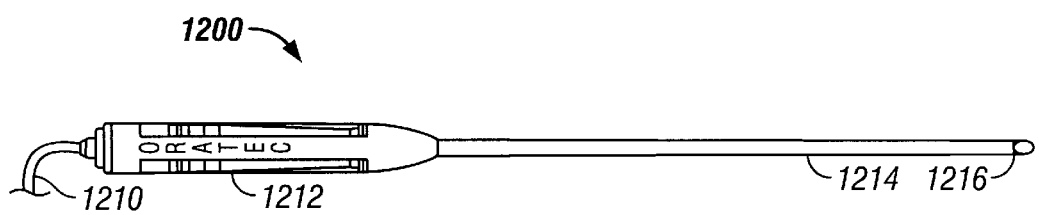

FIG. 1 illustrates a simplified view of an electrosurgical instrument 1200 and cannula 1202 according to an embodiment of the invention. FIG. 1A is an illustration of a conventional cannula 1202 utilized in one embodiment of the invention. Cannula 1202 consists of a guide 1224 with an opening 1226 at its distal end. Cannula 1202 is attached at its proximal end to introducer 1222. Instrument port 1228 is located at the proximal end for the introduction of the surgical probe. Cannula 1202 may also have an extension 1232 with a fluid port 1236. As illustrated in FIG. 1B, electrosurgical instrument 1200 consists of a handle 1212 to which is attached a power cord 1210, a probe shaft 1214, and a probe tip 1216. During introduction into the body, a blunt insert or obturator (not shown) is inserted through instrument port 1228. Cannula 1202 is inserted into the surgical site on the patient functioning as a trocar. Electrosurgical instrument 1200 is then inserted into cannula 1202 through instrument portal 1228 so that the tip 1216 protrudes from the opening 1226 in cannula 1202. Probe shaft 1214 is rigid and securely attached to the handle 1212 to allow a surgeon to maneuver the probe tip 1216 into a desired position and orientation without a guide.

Figure 1C:
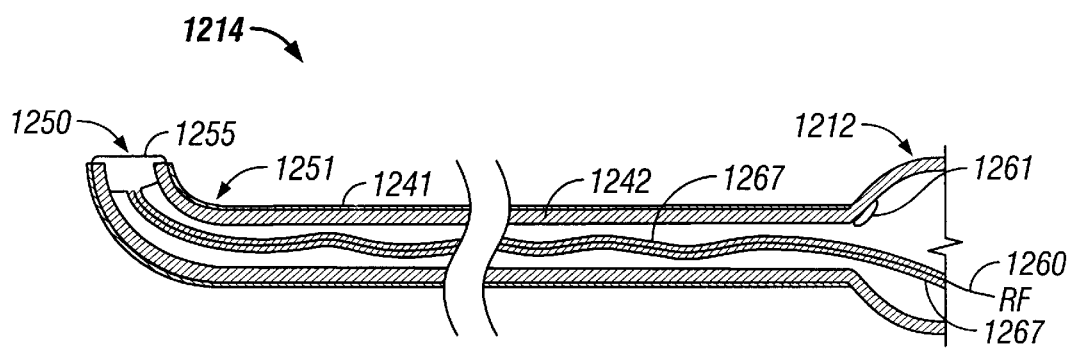
Figures 2A, 2B:
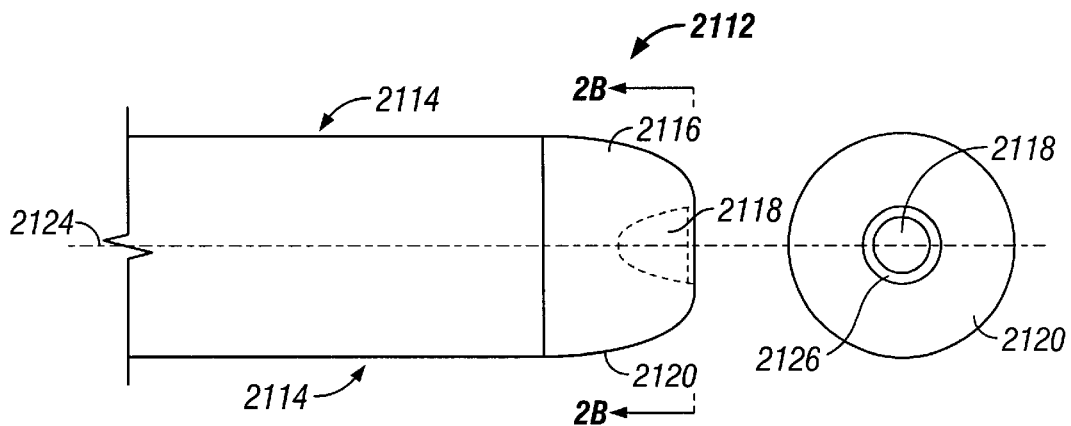
FIGS. 2A–2D are side, end, perspective, and cross-sectional side views of a probe tip for an electrosurgical instrument, according to an embodiment of the invention, wherein the probe tip has a volatization chamber formed therein, with FIG. 2B being taken along line 2B in FIG. 2A.
Figure 2C:
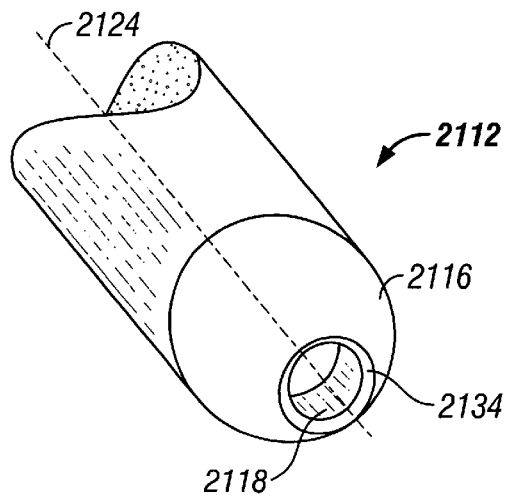
Figure 2D:
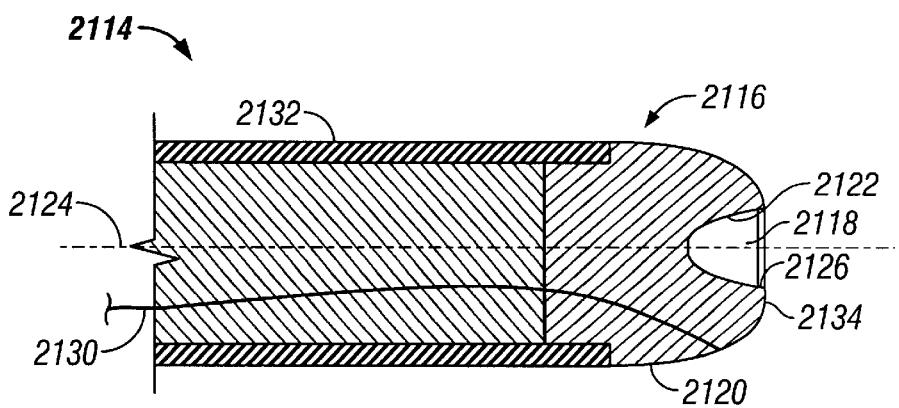
Figure 3C:
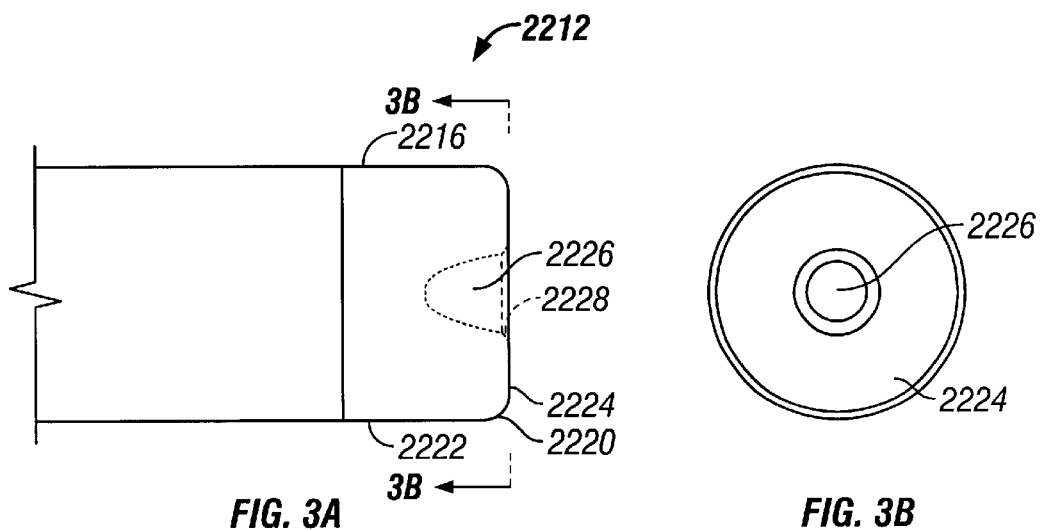
Figure 3C:
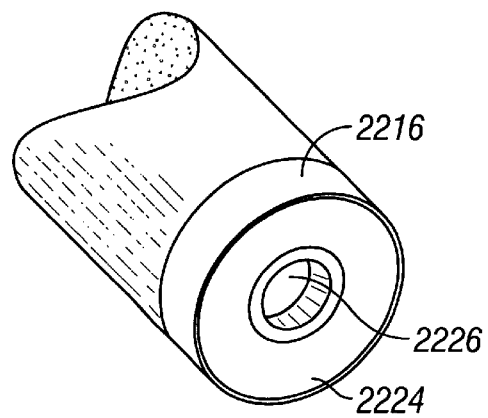
Figure 3D:
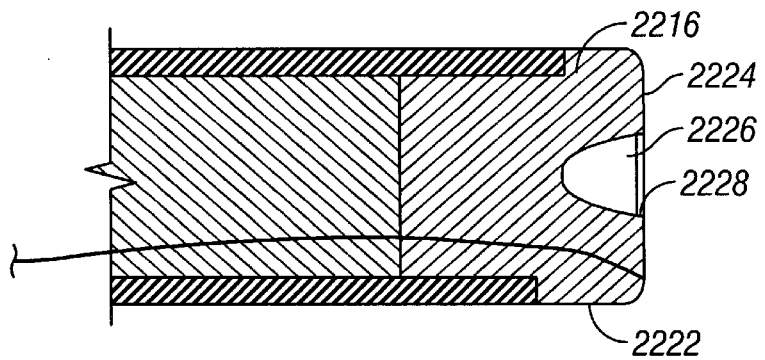

FIG. 1C illustrates a cross-sectional side view of the probe shaft 1214. Probe handle 1212 is connected to shaft tubing 1242. Shaft tubing insulator 1241 covers the shaft tubing 1242. The shaft tubing insulator 1241 may be any biocompatible material such as Teflon or any other suitable material such as nylon shrink tubing. Power wire 1260 is connected to a power supply (not shown) in the proximal portion of the probe and probe handle 1212. Power insulator 1267 covers and insulates power wire 1260. The power insulator 1267 material is preferably a tubing such as Teflon or polyimide, but may also include any other insulator material which would be known by a person skilled in the art, such as a coating. Power wire 1260 connects the power supply to an active electrode (not shown) on the distal energy application tip 1250. The power wire may be stainless steel, titanium, tungsten, copper, or any other compatible and suitable conductor. A return wire 1261 connects a return electrode (not shown in FIG. 1) to the power supply. The energy application tip 1250 has an energy application surface 1255. The energy application surface 1255 is configured to have a variety of configurations such as concave, convex, or concavo-convex for the delivery of thermal energy to the soft tissue site. Probe shaft tubing 1242 may also have a bent portion 1251 which may be configured for easier access to narrow or confined joint spaces.

FIGS. 2A–D illustrate a probe tip 2112 on an end of a probe shaft 2114, according to an embodiment of the invention. The probe tip 2112 includes an energy application tip or an electrode 2116 having a dimple or volatization chamber 2118 formed therein.

The electrode 2116 has a conductive outer surface 2120 and a conductive inner surface 2122. The surfaces 2120 and 2122 are formed symmetrically about an elongated axis 2124 of the probe shaft 2114. The outer surface 2120 forms a dome shape, and the inner surface 2122 forms a recess in a distal end of the electrode 2116. The volatization chamber 2118 is defined by the inner surface 2122 of the electrode 2116. The only passage into or out of the volatization chamber 2118 is through a mouth 2126 thereof.

An electric power conductor 2130 extends through the probe shaft 2114, and has an end which is attached to the outer surface 2120. The probe shaft 2114 has a nonconductive outer shell 2132, which prevents electric current from conducting between the electric power conductor 2130 and an area surrounding the probe shaft 2114. RF current can be provided through the electric power conductor 2130 to the outer surface 2120. The outer surface 2120 is electrically connected to the inner surface 2122, so that RF current is also provided to the inner surface 2122.

FIGS. 2E(i) to 21G(ii) illustrate how the electrode 2116 is used to create, grow, and eject vapor pockets, and thereby mobilize heated liquid that offsets convective cooling from the electrode 2116 to surrounding liquid.

A surgical port is formed into the body of a patient utilizing a cannula, and is partially defined by a surgical site 2136 within the body of the patient. The surgeon inserts the electrode 2116 into the surgical port and positions a face 2134 surrounding the mouth 2126 adjacent to the surgical site 2136. The surgical port is then filled with a liquid 2140, typically a saline solution, that covers the surgical site 2136. The liquid 2140 fills the areas around the outer surface 2120 and within the volatization chamber 2118.

RF current is then applied to the surfaces 2120 and 2122. In this embodiment, because the probe tip 2112 has a monopolar construction, the RF current conducts through the liquid 2140 and the body of the patient to ground. Alternatively, in a bipolar construction, the RF current conducts from the electrode 2116 and the tip 2112 to a separate return electrode located near the tip or on the probe shaft. The RF current heats an area adjacent to the outer surface 2120 and the inner surface 2122. The heat adjacent to the outer surface 2120 heats the surgical site 2136, and the heat adjacent to the inner surface 2122 heats the liquid in the volatization chamber 2118.

As shown in FIGS. 2E(i) and 2E(ii), the liquid within the volatization chamber 2118 expands and ultimately evaporates, creating one or more small bubbles or vapor pockets 2142 at a proximal surface of the volatization chamber 2118. The formation of the vapor pocket 2142 mobilizes liquid on a distal side thereof to move in a direction 2144 out of the volatization chamber 2118.

Further heating of the liquid within the volatization chamber 2118 causes further evaporation of the liquid. The vapor pocket or vapor pockets grow to form a larger vapor pocket 2142A, as illustrated in FIG. 2F(i). Growth of the vapor pocket 2142A expels the heated liquid in directions 2146 over a distal face of the electrode 2116. The heated liquid 2140 heats the face of the electrode. Any tendency for the electrode 2116 to convect heat to colder liquid passing over outer surfaces thereof is counteracted by the warm liquid flowing out of the volatization chamber 2118 over the face of the electrode. As illustrated in the cross-section of FIG. 2F(ii), the vapor pocket 2142A is entirely surrounded by the inner surface 2122, so that the vapor pocket 2142A is contained within the volatization chamber 2118 by inner surface 2122.

As illustrated in FIGS. 2G(i) and 2G(ii), the vapor pocket eventually grows into a larger vapor pocket 2142B, which ejects or eructs from the volatization chamber 2118 through the mouth 2126 out of the electrode 2116. The volatization chamber 2118 is simultaneously replenished with more of the liquid 2140 flowing in directions 2150 into the volatization chamber 2118. It is believed that eddy currents are created as cooler liquid rushes in to fill the volatization chamber 2118, and that the eddy currents assist in the heating and evaporation of the liquid in the volatization chamber 2118.

A continuous, thermodynamic pump effect is created, whereby the liquid continues to circulate over inner and outer surfaces of the probe tip 2112. Liquid is continuously heated in the volatization chamber 2118 and subsequently flows with the vapor pockets over outer surfaces of the probe tip 2112, thereby maintaining its temperature. A warmer probe tip 2112 allows for the probe tip 2112 to be held further away from the surgical site 2136 and thereby create a more even temperature profile over the surgical site 2136 with less searing. Continuous circulation of the liquid also clears the probe tip 2112 from any tissues that accumulate over the probe tip 2112 and especially inside the volatization chamber 2118.

The volatized liquid can also be used to regulate or modify the electrical power that is supplied to the electrode 2116. A vapor pocket between the electrode 2116 and the surgical site 2136 electrically insulates active surfaces of the electrode 2116 from the surgical site 2136 so that energy transfer from the electrode 2116 to the tissue of the surgical site 2136 is blocked off. The impedance rises when the energy transfer is blocked off, with a corresponding reduction in electric power delivered to the electrode 2116 by a generator.

FIGS. 3A–D illustrate a probe tip 2212 according to another embodiment of the invention. The probe tip 2212 includes an electrode 2216 having an outer surface 2220. The outer surface 2220 has a cylindrical outer portion 2222 and a front face 2224, which is flat. A volatization chamber 2226 is formed into the face 2224. The volatization chamber has a mouth 2228, having a diameter which is approximately half the outer diameter of the face 2224. A more even temperature profile can be created adjacent to the surgical site with the face 2224, because the face 2224 more accurately reflects the profile of the surgical site.

FIGS. 4A–D illustrate a probe tip 2310, according to a further embodiment of the invention. The probe tip 2310 has an electrode 2312, having a first volatization chamber 2314 and a second volatization chamber 2316 formed in a front face 2318 thereof. The second volatization chamber 2316 has a separate mouth than the first volatization chamber 2314. The second volatization chamber 2316 is in the form of a ring that entirely surrounds the first volatization chamber 2314.

Figure 4C:
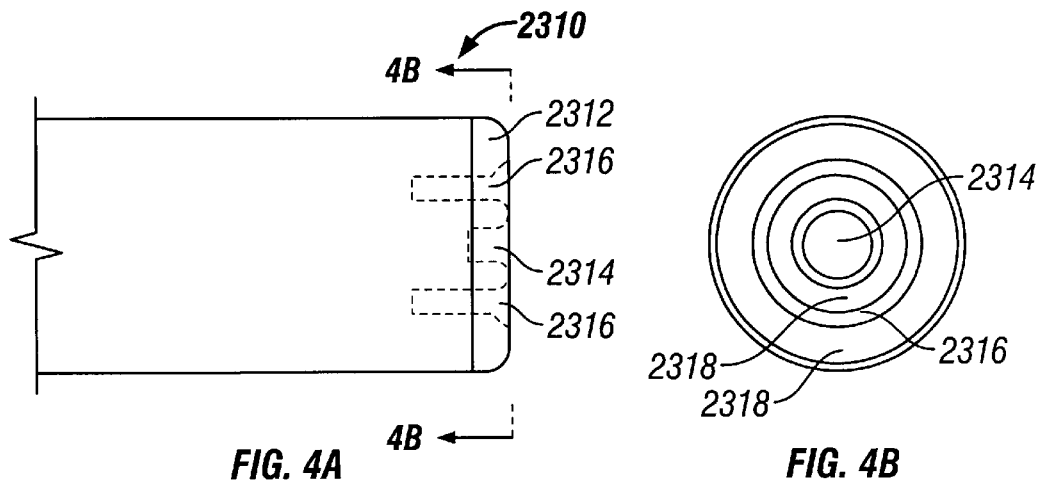
Figure 4C:
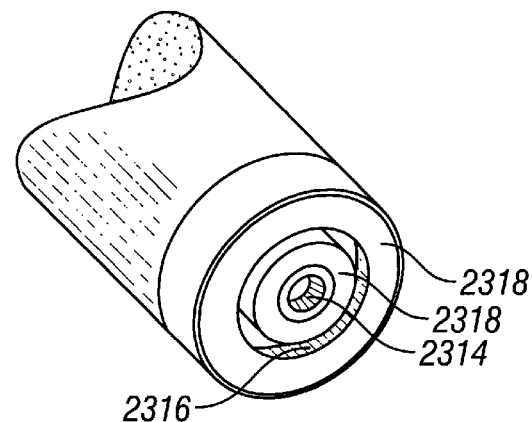
Figure 4D:
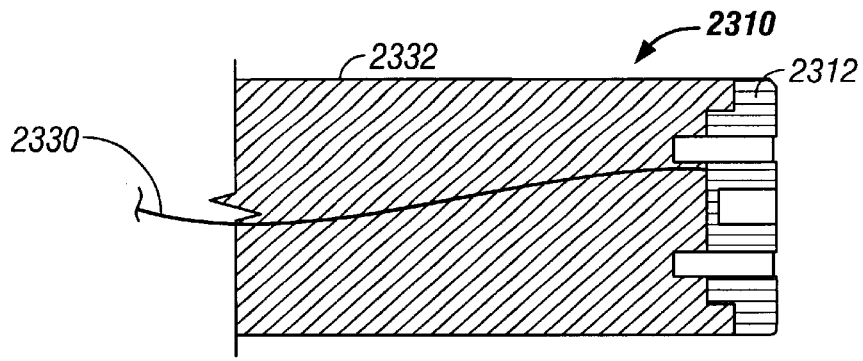
Figure 4E:
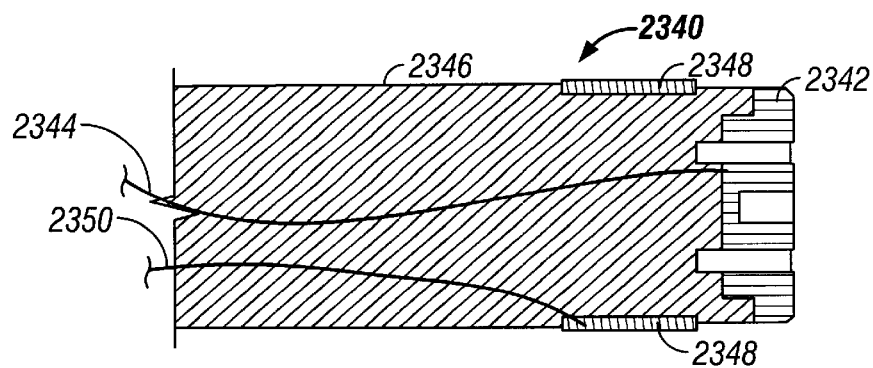

As illustrated in FIG. 4D, an electric power conductor 2330 extends through a probe shaft 2332, and is attached to the electrode 2312. The probe tip 2310 thus has a monopolar construction. FIG. 4E illustrates a probe tip 2340 having a bipolar construction. As in the embodiment of FIG. 4D, the probe tip 2340 has an electrode 2342 and an electric power conductor 2344 extending through a probe shaft 2346 to the electrode 2342. In addition, the probe tip 2340 also has a cylindrical ground terminal 2348 located distally relative to the electrode 2342 around the shaft 2346. An electric ground conductor 2350 extends through the probe shaft 2346, and is attached to the terminal 2348. As will be understood from the aforegoing description, the liquid electrically connects the electrode 2342 with the terminal 2348, so that RF current provided through the electric power conductor 2344 conducts through the liquid, the terminal 2348, and the electric current conductor 2350 to ground.

Figure 5A:
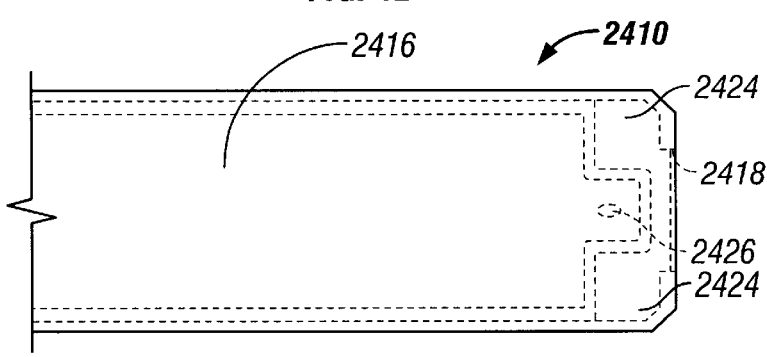
FIGS. 5A–C are side, perspective, and cross-sectional side views of a probe tip having a volatization chamber within a ground terminal.
Figure 5B:
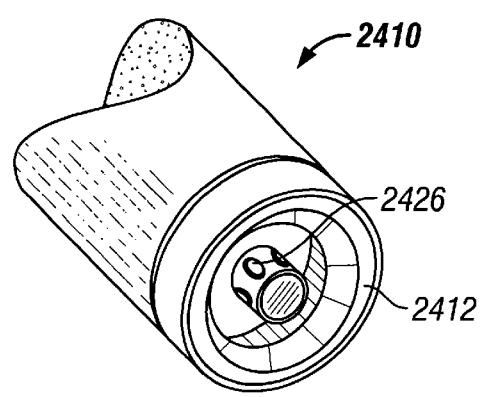
Figure 5C:
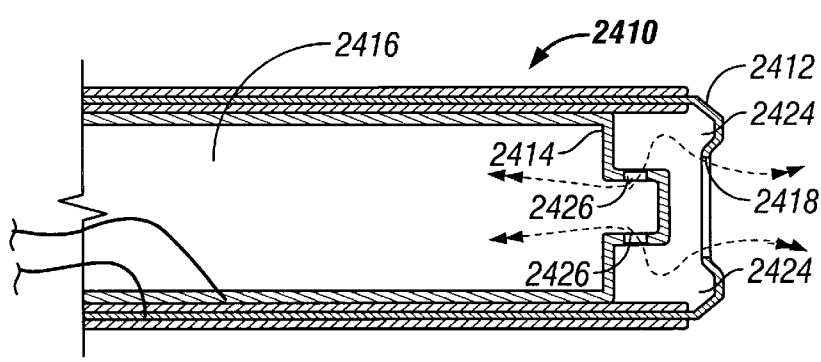

FIGS. 5A–C illustrate a probe tip 2410, according to a further embodiment of the invention, which allows generation of more vapor pockets. The probe tip 2410 is also of bipolar construction. The probe tip 2410 has an electrode 2412 and a ground terminal 2414. The ground terminal 2414 forms an internal first chamber 2416. A liquid can flow through a mouth 2418 into a second chamber 2424, and then through openings 2426 in the ground terminal 2414 into the first chamber 2416. RF current provided to the electrode 2412 conducts through the liquid in the second chamber 2424 to the ground terminal 2414. The RF current in the ground terminal 2414 then heats the liquid in the first chamber 2416. Volatized liquid and vapor pockets eject from the first chamber 2416 through the openings 2426 into the second chamber 2424. More liquid will then be volatized within the second chamber 2424. Volatized liquid and vapor pockets are then ejected through the mouth 2418 out of the probe tip 2410. Colder liquid simultaneously enters the second chamber 2424 through the mouth 2418 and flows from the second chamber 2424 through the openings 2426 into the first chamber 2416.

FIGS. 6A–D illustrate probe tips 2510, 2520, and 2530 according to further embodiments of the invention. In each embodiment, a volatization chamber 2540 has an inner portion 2544, having a larger cross-sectional area than a mouth 2546 of the volatization chamber 2540. Due to the larger cross-sectional area and therefore larger volume of the internal portion 2544, larger vapor pockets are created before they are ejected through the mouth 2546.

Figure 6A:
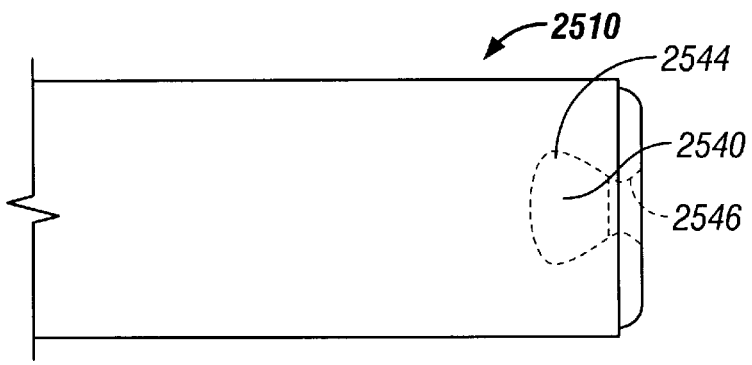
FIGS. 6A–D are side and cross-sectional side views of three different probe tips having vapor pocket chambers with larger cross-sections than mouths out of their vapor pocket chambers.
Figure 6B:
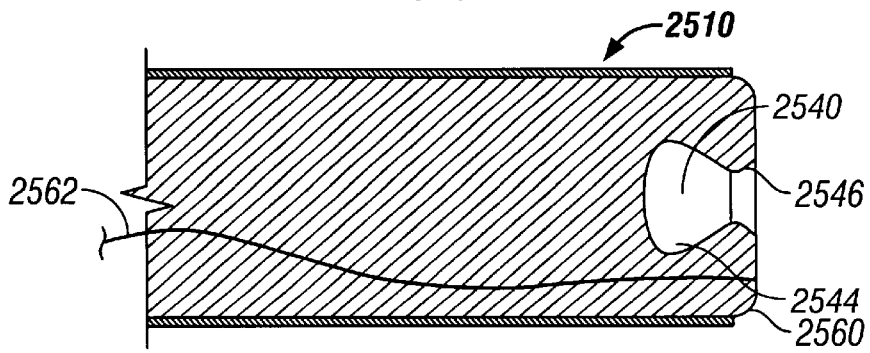
Figure 6C:
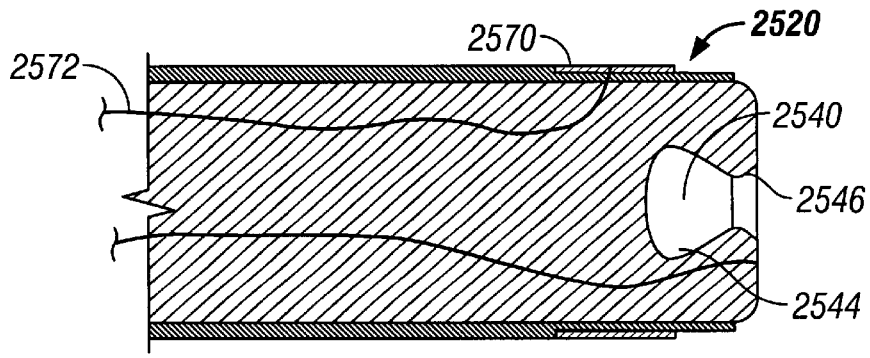
Figure 6D:
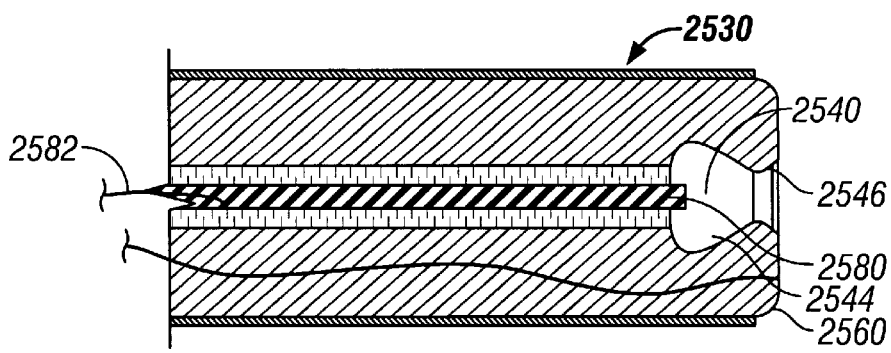

The probe tip 2510 of FIGS. 6A and 6B has an electrode 2560 and an electric power conductor 2562 connected thereto. The probe tip 2510 has a monopolar construction. The probe tips 2520 and 2530 of FIGS. 6C and 6D, respectively, have bipolar constructions. The probe tip 2520 has an external ground terminal 2570 and an electric ground conductor 2572 connected thereto. The probe tip 2530 has an internal ground terminal 2580. A front portion of the ground terminal 2580 is located within the volatization chamber 2540, and a rear portion of the terminal 2580 forms a ground conductor 2582. The electrode 2560 of the probe tip 2530 is located on an external surface only, i.e., not also on internal surfaces of the volatization chamber 2540 of the probe tip 2530. The electrode 2560 is thus electrically disconnected from the terminal 2580. Electric current can conduct between the electrode 2560 and the terminal 2580 through liquid in the volatization chamber 2540.

FIGS. 7A–D illustrate probe tips 2610 and 2620 according to further embodiments of the invention. The probe tip 2610 of FIGS. 7A–C includes an electrode shell 2622, an outer insulator 2624, and an inner insulator plug 2626. The electrode shell 2622 has a cylindrical portion 2628, and a front face portion 2630. The plug 2626 is located within the cylindrical portion 2628. A front face of the plug 2626 is spaced from the face portion 2630 of the electrode 2622. A volatization chamber 2634 is defined by inner surfaces of the front face portion 2630, the cylindrical portion 2628, and the front face of the plug 2626, jointly. The front face portion 2630 is formed into a conical depression 2640 having a peripheral surrounding rim 2642. Openings 2650 form mouths out of the chamber 2634 into the area surrounded by the conical depression 2640. Vapor pockets created within the chamber 2634 are ejected through the openings 2650. The rim 2642 may be located relatively close to a surgical site, so that volatized fluid from the vapor pockets is contained within the conical depression 2640.

Figure 7A:
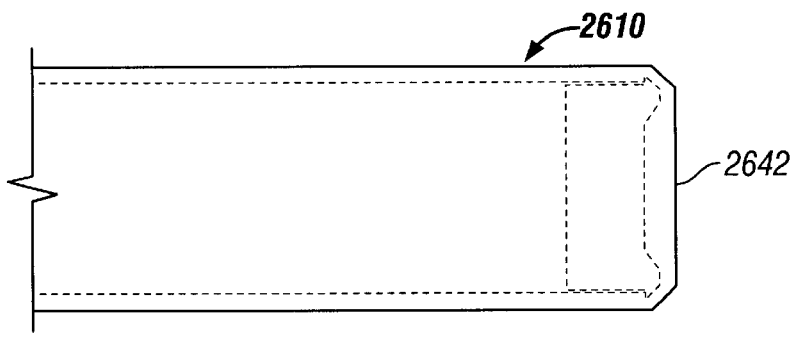
FIGS. 7A–D are side, perspective, and cross-sectional side views of two probe tips having a front face with a conical depression therein.
Figure 7B:
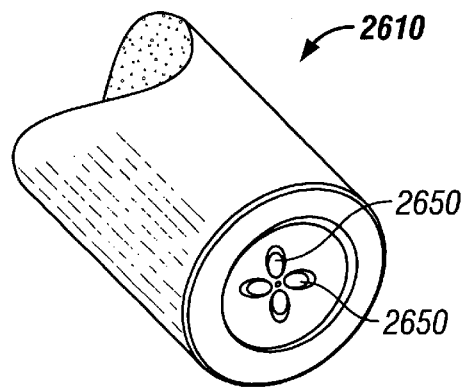
Figure 7C:
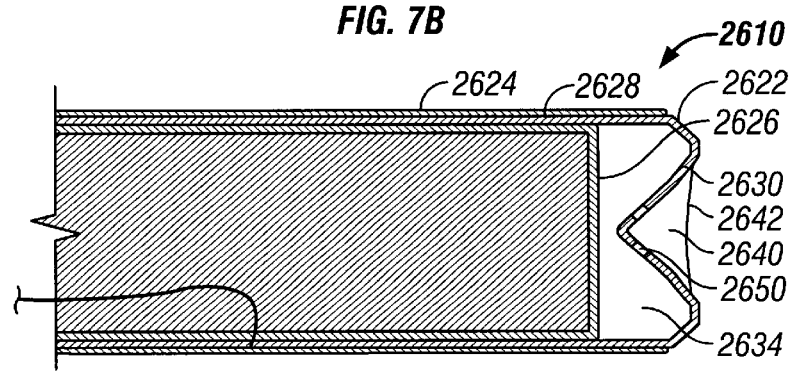
Figure 7D:
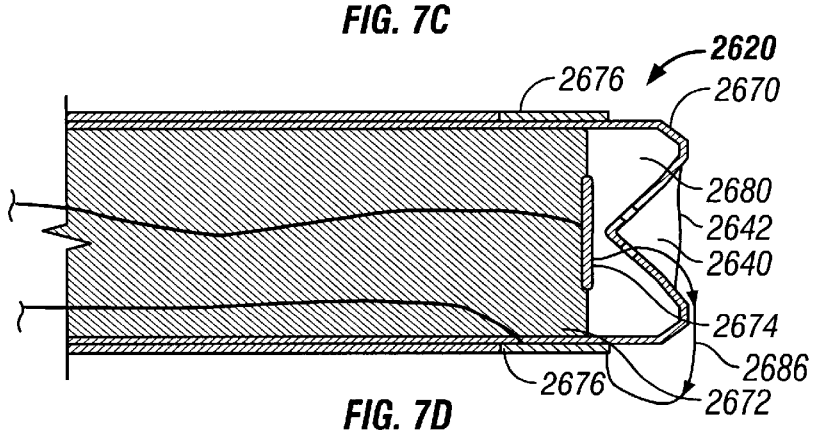
Figures 8A, 8B:
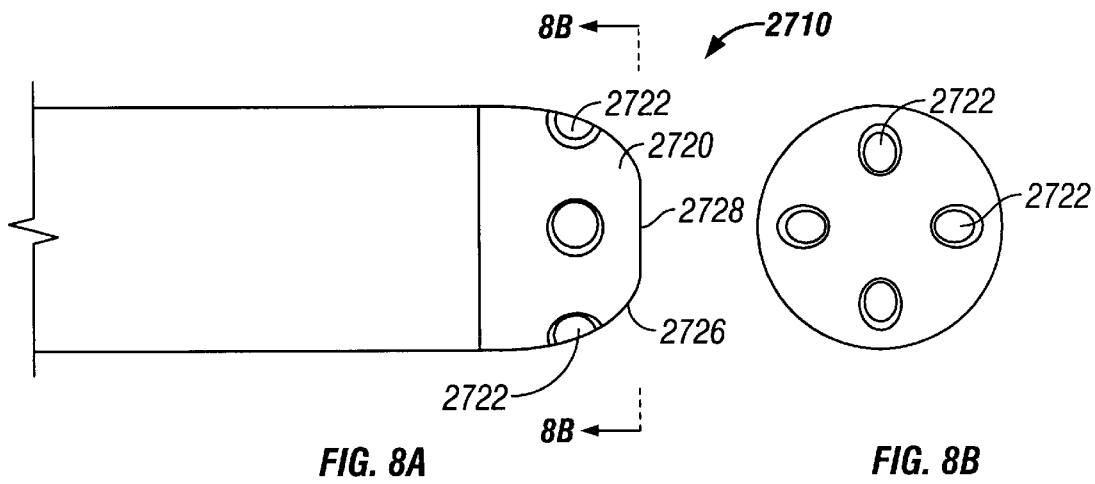
FIGS. 8A–D are side, end, perspective, and cross-sectional side views of a probe tip having shallow vapor pocket chambers in a domed portion of an external surface of an electrode, with FIG. 8B being taken along line 8B in FIG. 8A.
Figure 8C:
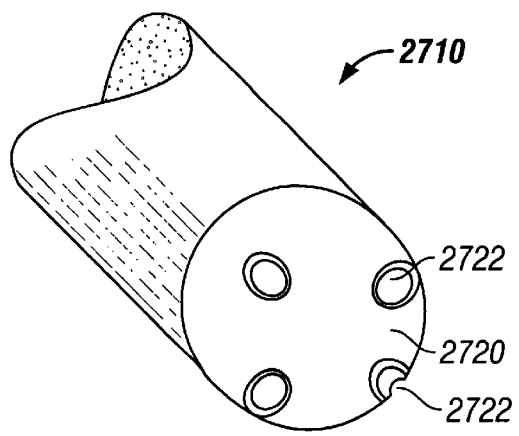
Figure 8D:
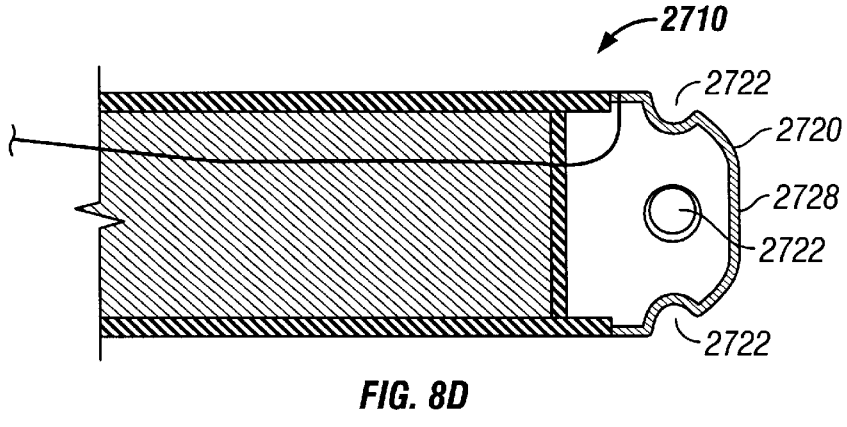

The probe tip 2620 of FIG. 7D includes a nonconductive shell 2670, a nonconductive plug 2672, an electrode 2674, and a ground terminal 2676. The nonconductive shell 2670 has the same shape as the conductive electrode shell 2622 of the probe tip 2610 of FIGS. 7A–C. The nonconductive shell 2670 defines an internal chamber 2680, together with the plug 2672. The electrode 2674 is located on a face of the plug 2672, and has a face that is exposed into the internal chamber 2680. The ground terminal 2676 is positioned around a cylindrical portion of the nonconductive shell 2670. The electrode 2674 is electrically connected through a fluid along a path 2686. The path 2686 passes through the chamber 2680 to volatize liquid within the chamber 2680 to generate vapor pockets. The path 2686 also passes over an external surface of the nonconductive shell 2670 to create heat that treats a surgical site.

FIGS. 8A–D illustrate a probe tip 2710, having an electrode 2720 with shallow vapor pocket chambers 2722. The electrode 2720 has an outer surface with a dome-shaped portion 2726 and a front face 2728 which is flat. The chambers 2722 are all formed in the dome-shaped portion 2726. Either the dome-shaped portion 2726 or the face 2728 may be positioned adjacent to the surgical site. Should the dome-shaped portion 2726 be located against the surgical site, the vapor pockets will be ejected out of one or more of the chambers 2722 toward the surgical site.

FIGS. 9A–F illustrate probe tips 2810 and 2820, according to yet further embodiments of the invention, each having two vapor pocket chambers 2830 and 2832 that are interconnected with one another. The probe tip 2810 of FIGS. 9A–C has a nonconductive shell 2836, and a conductive electrode 2838. The nonconductive shell 2836 has a cylindrical portion 2842 and a front portion 2844. A ring-shaped depression 2850 is formed in the front portion 2844. An internal volume 2852 is formed jointly by the front portion 2844, the cylindrical portion 2842, and the electrode 2838. The depression 2850 divides the internal volume 2852 into the central chamber 2830 and the outer chamber 2832. The outer chamber 2832 is in the form of a ring around the central chamber 2830. The chambers 2830 and 2832 are in communication with one another because of an annular spacing 2860 between the depression 2850 and the electrode 2838. The chamber 2832 acts as a reservoir of vapor. The vapor is ultimately expelled from the chamber 2832 through the spacing 2860 and the chamber 2830 and then through a mouth 2870 out of the probe tip 2810.

The probe tip 2810 has a monopolar construction. Current conducts from the electrode 2838 through the chamber 2830 and the mouth 2870 to a body of a patient. The probe tip 2820 of FIG. 9D has a bipolar construction. The probe tip 2820 is the same as the probe tip 2810, except that a ground terminal 2880 is located around the cylindrical portion 2842. Current conducting through the mouth 2870 can conduct around the nonconductive shell 2836 to the ground terminal 2880.

Figure 9A:
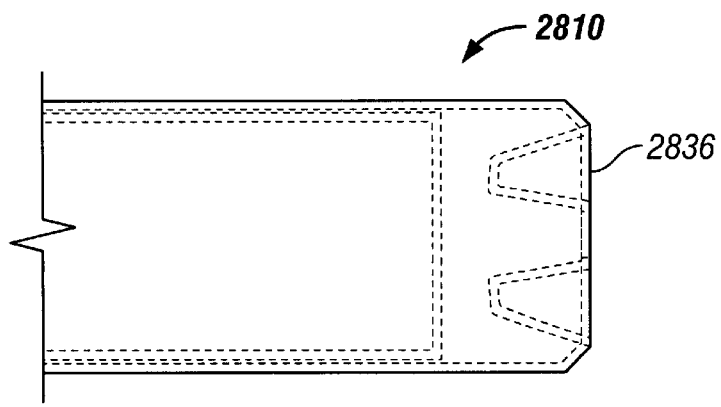
FIGS. 9A–F are side, perspective, and cross-sectional side views of two probe tips, each having two vapor pocket chambers in communication with one another.
Figure 9B:
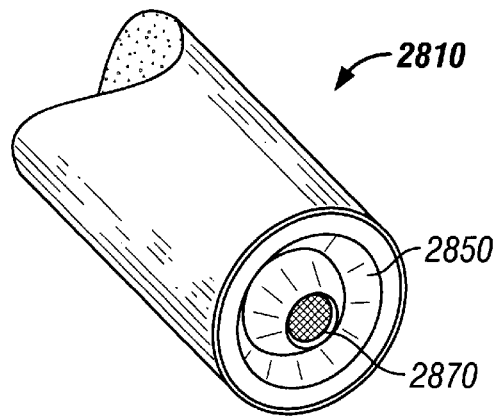
Figure 9C:
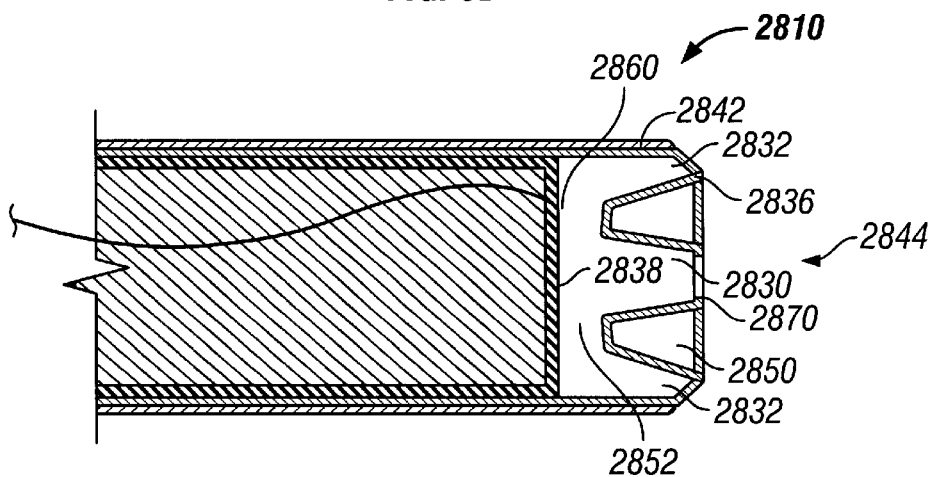
Figure 9D:
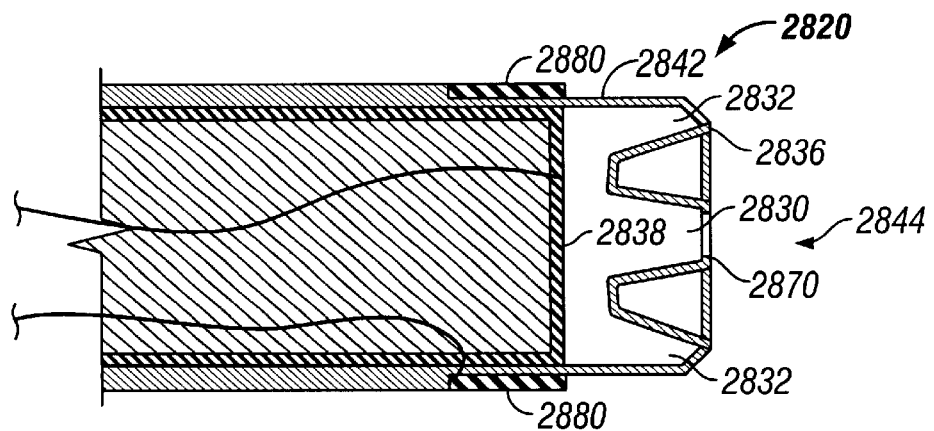
Figure 9E:
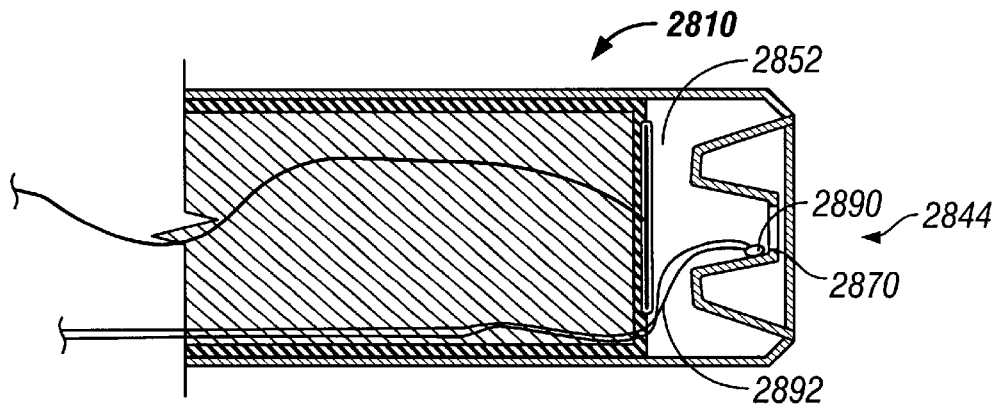
Figure 9F:
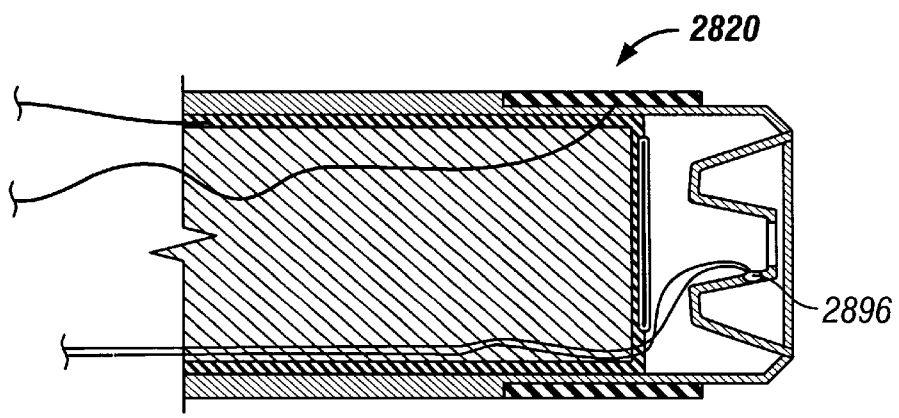
Figures 10A, 10B:
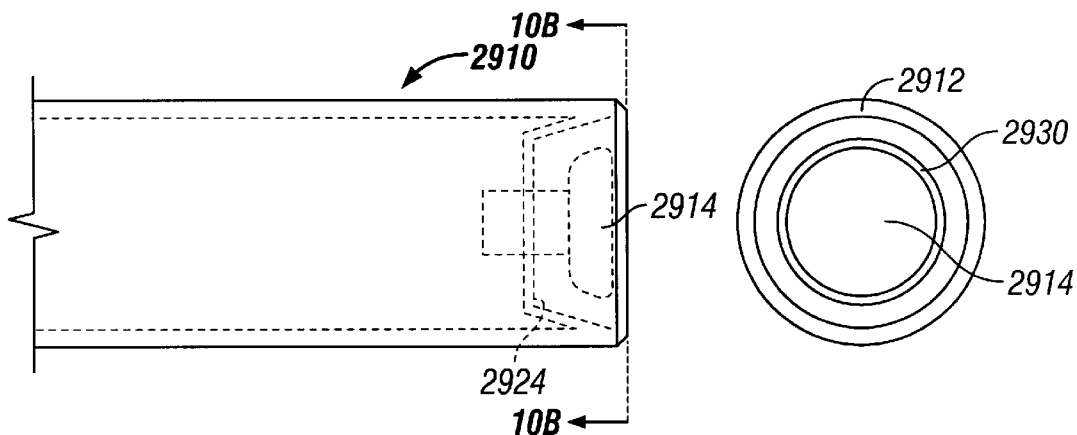
FIGS. 10A–D are side, end, perspective, and cross-sectional side views of a probe tip having an electrode which is secured through a fastener so that an area around the fastener forms a volatization chamber, with FIG. 10B being taken along line 10B in FIG. 10A.
Figure 10C:
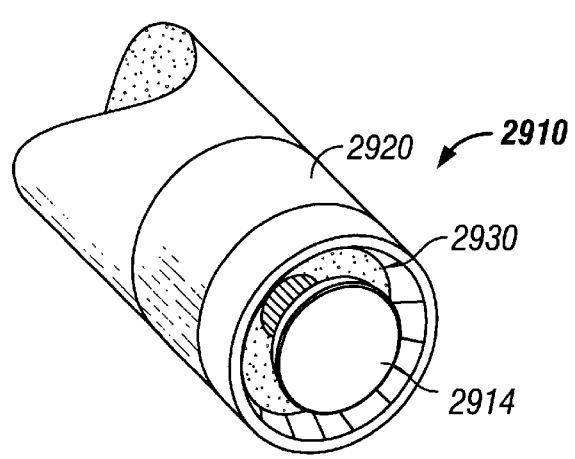
Figure 10D:
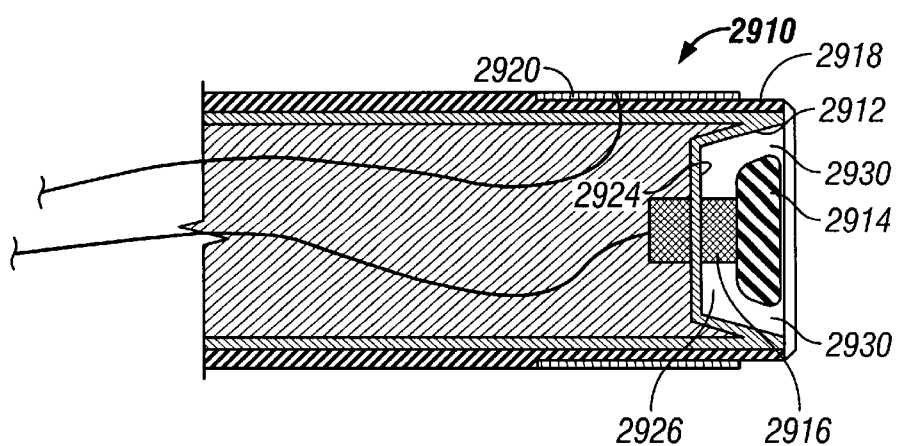

Thermocouples may be connected to the probe tips described herein. FIG. 9E, for example, illustrates the probe tip 2810 of FIGS. 9A–C, which further has a thermocouple 2890 with thermocouple wires 2892. The thermocouple 2890 is attached to the front portion 2844 near the mouth 2870. The thermocouple wires 2892 extend from the thermocouple 2890 through the internal volume and through the probe shaft to the handle. FIG. 9F illustrates a thermocouple 2896 attached to the probe tip 2820 of FIG. 9D in a similar manner.

FIGS. 10A–D illustrate a probe tip 2910 according to a further embodiment of the invention. The probe tip 2910 includes a shell portion 2912, one electrode 2914, a fastener 2916, a nonconductive coating 2918, and a ground terminal 2920. The shell portion 2912 has a depression formed in a front portion 2924 thereof. The fastener 2916 is secured to a center of the front portion 2924. The electrode 2914 is secured to the fastener 2916 and a portion of the fastener 2916 spaces the electrode 2914 from the front portion 2924. As such, an annular chamber 2926 is defined around the portion of the fastener 2916 that spaces the electrode 2914 from the front portion 2924. An annular mouth 2930 is defined between an outer surface of the electrode 2914 and an inner surface of the shell portion 2912. Vapor pockets eject from the chamber 2926 through the annular mouth 2930. The nonconductive coating 2918 is formed around a cylindrical portion of the shell portion 2912. The ground terminal 2920 is located around the nonconductive coating 2918. Current can conduct through a liquid between the electrode 2914 and the ground terminal 2920.

Figure 11C:
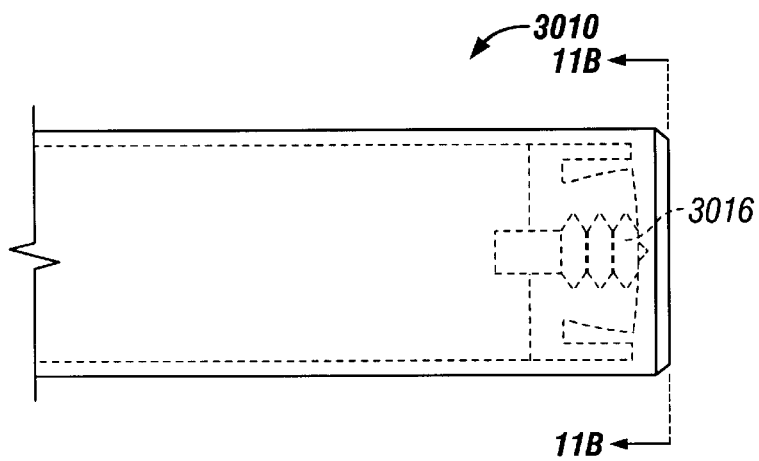
Figure 11C:
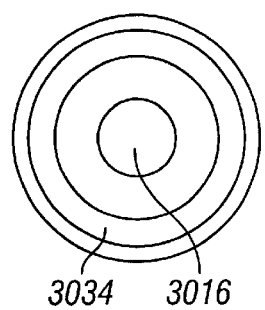
Figure 11C:
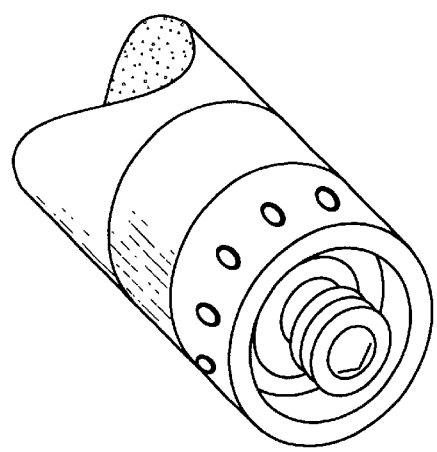
Figure 11D:
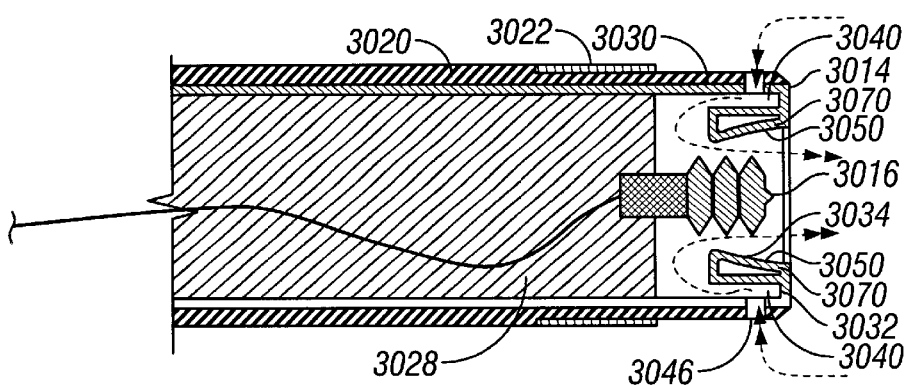

FIGS. 11A–B illustrate a probe tip 3010 that includes structures and features that promote unidirectional flow through a chamber 3012. The probe tip 3010 includes a frame portion 3014, electrodes 3016, a nonconductive coating 3020, and a ground terminal 3022. The frame portion 3014 includes an inner portion 3028, a cylindrical outer portion 3030, an annular face portion 3032, and an annular divider portion 3034. The inner portion 3028 is located inside the outer portion 3030. The annular face portion 3032 has an outer edge located at the outer portion 3030 and extends inwardly therefrom. The annular face portion 3032 is spaced from a face of the inner portion 3028. The annular divider portion 3034 extends inwardly from an inner edge of the face portion 3032 toward the inner portion 3028. An annular ring-shaped chamber 3040 is formed jointly by the annular divider portion 3034, the annular face portion 3032, and the outer portion 3030. Liquid entry openings 3046 are formed through the outer portion 3030 into the chamber 3040. The annular divider portion 3034 has an inner surface 3050, and the electrodes 3016 are mounted within the inner surface 3050. The electrodes 3016, in cross-section, have a corrugated profile which increases fluid resistance. Liquid enters through the liquid entry passages 3046 into the chamber 3048, and then flows into a region between the electrodes 3016 and the surface 3050 of the annular divider portion 3034. The liquid is there evaporated into vapor pockets that are ejected through a mouth 3070 formed by an inner edge of the annular face portion 3032. More liquid then enters through the liquid entry passages 3046. It can thus be seen that unidirectional flow can be maintained with the features and structures of the probe tip 3010, in particular the corrugated profile of the electrodes 3016.

While certain exemplary embodiments have been described and shown in the accompanying drawings, it is to be understood that such embodiments are merely illustrative and not restrictive of the current invention, and that this invention is not restricted to the specific constructions and arrangements shown and described since modifications may occur to those ordinarily skilled in the art.

What is claimed:

1. An electrosurgical instrument, comprising:
    a holding formation;
    a probe shaft secured to the holding formation and having an elongated section extending therefrom;
    an electric conductor extending along the elongated section; and
    a probe tip on a distal end of the probe shaft opposing the holding formation, the probe tip defining at least a first volatization chamber with a mouth out of the probe tip, and including at least one electrode to which RF current is provided through the electric conductor, the electrode heating an area adjacent to the probe tip and a liquid in the first volatization chamber to evaporate the liquid into a vapor pocket that ejects from the first volatization chamber through the mouth out of the probe tip, creating a thermodynamic flow of the liquid in front of the vapor pocket.

2. The electrosurgical instrument of claim 1, wherein the holding formation is a handle.

3. The electrosurgical instrument of claim 2, wherein the probe shaft is substantially rigid to allow a surgeon, holding the handle, to move the probe tip into position without a guide.

4. The electrosurgical instrument of claim 1, wherein the electric conductor is attached to the electrode.

5. The electrosurgical instrument of claim 1, wherein an inner surface of the electrode defines the volatization chamber.

6. The electrosurgical instrument of claim 1, wherein at least one cross-section through the probe tip and the volatization chamber shows no openings out from the volatization chamber out of the probe tip.

7. The electrosurgical instrument of claim 1, wherein the electrode has an exposed outer surface around the volatization chamber.

8. The electrosurgical instrument of claim 7, wherein the exposed outer surface entirely surrounds the volatization chamber.

9. The electrosurgical instrument of claim 7, wherein an inner surface of the electrode defines the volatization chamber.

10. The electrosurgical instrument of claim 1, wherein the electrode has a front face around the mouth.

11. The electrosurgical instrument of claim 10, wherein the front face entirely surrounds the mouth.

12. The electrosurgical instrument of claim 1, wherein the volatization chamber has a larger cross-sectional area than the mouth.

13. The electrosurgical instrument of claim 1, wherein the electrode is a power electrode, the probe tip further including a ground electrode electrically connected to the power electrode through more of the liquid.

14. The electrosurgical instrument of claim 1, wherein growth of the vapor pocket expels liquid heated in the volatization chamber through the mouth and over an external face of the probe tip to heat the face, and the volatization chamber is replenished with more liquid when the vapor pocket ejects from the volatization chamber.

15. The electrosurgical instrument of claim 13, further comprising:
    a ground conductor extending along the elongated section and electrically attached to the ground electrode.

16. The electrosurgical instrument of claim 1, further comprising:
    a thermocouple attached to the probe tip; and
    a thermocouple wire extending from the thermocouple along the elongated section.

17. The electrosurgical instrument of claim 1, wherein the probe tip has at least a second volatization chamber therein.

18. The electrosurgical instrument of claim 17, wherein the electrode heats more of the liquid in the second volatization chamber.

19. The electrosurgical instrument of claim 17, wherein the second volatization chamber has a separate mouth out of the probe tip than the first volatization chamber.

20. The electrosurgical instrument of claim 19, wherein the second volatization chamber is a ring around the first volatization chamber.

21. An electrosurgical instrument, comprising:
    a holding formation;
    a probe shaft secured to the holding formation and having an elongated section extending therefrom;
    an electric conductor extending along the elongated section; and
    a probe tip on a distal end of the probe shaft opposing the holding formation, the probe tip including an electrode to which RF current is provided through the electric conductor, the electrode having an exposed face with at least a first recessed volatization chamber formed therein.

22. The electrosurgical instrument of claim 21, wherein the probe tip has at least a second recessed volatization chamber therein.

23. A method of treating a surgical site within a body of a patient, comprising:
    inserting a probe tip into a surgical port formed in the body of the patient until the probe tip is positioned adjacent to the surgical site;
    at least partially filling the surgical port with a liquid, the liquid entering a volatization chamber in the probe tip; and
    providing RF current to an electrode of the probe tip to heat an area adjacent to the probe tip and the liquid in the volatization chamber, the liquid in the volatization chamber evaporating into a vapor pocket which ejects through a mouth of the volatization chamber out of the probe tip, creating a thermodynamic flow of the liquid in front of the vapor pocket.

24. The method of claim 23, wherein growth of the vapor pocket expels liquid heated in the volatization chamber through the mouth and over an external face of the probe tip to heat the face, and the volatization chamber is replenished with more liquid when the vapor pocket ejects from the volatization chamber.

25. The method of claim 24, wherein at least one cross-section through the probe tip and the volatization chamber shows no openings out from the volatization chamber out of the probe tip.

* * * * *